(12) United States Patent
Chassot

(10) Patent No.: US 6,203,909 B1
(45) Date of Patent: Mar. 20, 2001

(54) COMPOSITE PIGMENT

(75) Inventor: Laurent Chassot, Praroman (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/005,155

(22) Filed: Jan. 9, 1998

(30) Foreign Application Priority Data

Jan. 9, 1997 (CH) .................................................. 0037/97

(51) Int. Cl.[7] .............................. B32B 5/16; C09B 67/50; C08K 5/00
(52) U.S. Cl. ........................ 428/403; 106/410; 106/411; 106/493; 106/494; 106/499
(58) Field of Search ................................ 427/212, 213.3, 427/213.31, 214, 215, 218, 220, 222; 428/363, 402, 402.24, 403, 404, 323, 324, 331, 361; 106/600, 626, 638, 400, 415, 417, 436, 438, 481, 482, 499

(56) References Cited

U.S. PATENT DOCUMENTS

| | | | |
|---|---|---|---|
| 4,026,721 | * 5/1977 | Kurrle | 106/288 B |
| 4,458,073 | * 7/1984 | Marraccini et al. | 546/14 |
| 4,568,493 | * 2/1986 | Marraccini et al. | 260/245.74 |
| 4,585,864 | * 4/1986 | Marraccini et al. | 546/14 |
| 4,880,472 | 11/1989 | Bugnon et al. | 106/493 |
| 4,952,245 | 8/1990 | Iwano et al. | 106/404 |
| 5,037,475 | 8/1991 | Chida et al. | 106/403 |
| 5,116,418 | * 5/1992 | Kaliski | 106/419 |
| 5,208,111 | 5/1993 | Decher et al. | 428/420 |
| 5,219,660 | * 6/1993 | Wason et al. | 428/403 |
| 5,262,239 | * 11/1993 | Wason et al. | 428/403 |
| 5,312,484 | * 5/1994 | Kaliski | 106/446 |
| 5,312,485 | * 5/1994 | Wason et al. | 106/467 |
| 5,338,354 | * 8/1994 | Melville et al. | 106/442 |
| 5,344,487 | * 9/1994 | Whalen-Shaw | 106/416 |
| 5,346,546 | * 9/1994 | Kaliski | 106/436 |
| 5,449,402 | * 9/1995 | Whalen-Shaw | 106/416 |
| 5,454,864 | * 10/1995 | Whalen-Shaw | 106/416 |
| 5,458,680 | * 10/1995 | Shurling, Jr. et al. | 106/487 |
| 5,509,960 | * 4/1996 | Simpson et al. | 106/437 |
| 5,554,215 | * 9/1996 | Simpson et al. | 106/436 |
| 5,643,974 | * 7/1997 | Simpson et al. | 523/334 |
| 5,672,201 | * 9/1997 | Simpson et al. | 106/447 |
| 5,690,728 | * 11/1997 | Ravishankar | 106/416 |
| 5,755,870 | * 5/1998 | Ravishankar | 106/438 |
| 5,869,559 | * 2/1999 | Simpson et al. | 524/497 |
| 5,900,050 | * 5/1999 | Hayden et al. | 106/493 |

FOREIGN PATENT DOCUMENTS

| | | |
|---|---|---|
| 4225031 | 2/1994 | (DE) . |
| 4225357 | 2/1994 | (DE) . |
| 0278633 | 8/1988 | (EP) . |
| 0367236 | 5/1990 | (EP) . |
| 700976 A2 | * 3/1996 | (EP) . |

OTHER PUBLICATIONS

Cooper et al., Langmuir, 1995, 11, pp. 2713–2718.
Derwent Abst. 94–043831/06.
Derwent Abst. 94–043708/06
J. Phys. Chem., 1988, 92, pp. 2597–2601.
J. Am. Chem. Soc., 1988, 110, pp. 618–620.
J. Am. Chem. Soc., 1993, 115, pp. 11855–11862.

* cited by examiner

*Primary Examiner*—Paul Thibodeau
*Assistant Examiner*—Sheeba Ahmed
(74) *Attorney, Agent, or Firm*—Kevin T. Mansfield; David R. Crichton

(57) ABSTRACT

A composite pigment, which consists of a colourant and a substrate, using a substrate (S) and a colourant (C), which are each coated with ions or ionisable compounds having a charge rotating in the same direction, and, if desired, of additional ions or ionisable compounds having a change rotating in the same direction as layer material (L), wherein either (I) the sign of the change of the coating of S, or the sign of the charge of the coating of S and of the charge of L, which is the same, is opposite to that of charge of the coating of C, or (II) the sign of charges of the coatings of S and C is the same and is opposite to that of the charge of L.

12 Claims, No Drawings

COMPOSITE PIGMENT

The present invention relates to a composite pigment consisting of a substrate and a colourant.

This invention also relates to a process for the preparation of the composite pigments according to this invention, to their use for mass colouring high molecular weight organic material, for the preparation of paint systems, printing inks and inks, as well as to mass-coloured high molecular weight organic material.

In Langmuir 1995, 11, p. 2713–2718, Cooper et al. describe dye systems which are composed of several layers, where layers of congo red anions or copper phthalocyanine anions and of cationic polypeptides or copper phthalocyanine cations are alternately applied to a positively charged glass layer. Disadvantages are the elaborate method of preparation involving the layer-wise application of the differently charged compounds and also the restriction of the substances used to ionic dyes or dyes which can be correspondingly modified. In addition, the colour intensity is impaired by the intermediate layers between the monomolecular layers of the desired dye.

EP-A 472 990 describes substrate-layer systems where the uni- or multilayered layer elements consist of organic materials which are applied to the modified substrates by salt formation. Organic materials used are either monomeric substances carrying two ionic or ionisable functional groups having a charge rotating in the same direction, or polymers carrying a multitude of ionic or ionisable functional groups having a charge rotating in the same direction (polyelectrolytes). These systems have the disadvantage that (a) only (soluble) dyes can be used and that (b) these dyes can only be covalently bound to the organic materials.

DE-A 42 25 357 describes luster pigments based on substrates in platelet form and on chemically modified dyes carrying at least one basic functional group. Precondition for this process is the acid-solubility of the modified dyes. The modified dye is applied to the substrate by precipitation by neutralising the acid to reduce the acid-solubility of the dye. This process has the disadvantage that (a) only acid-soluble dyes can be used; (b) the acid must be neutralised (disposal problem and additional processing step); (c) the dye must carry a basic functional group; (d) the particle size cannot be controlled because of the precipitation; (e) the amount of adsorbed colourant in the substrate is not concentrated enough for some fields of application.

DE-A 42 25 031 describes the preparation of luster pigments carried out by applying an organic pigment, which can be dissolved undecomposed in a solvent, by precipitation to an inorganic substrate, a second solvent being added which is able to reduce the solubility of the organic pigment in the first solvent. The disadvantages of this process are (a) the use of solvent-soluble organic pigments; (b) the use of at least two solvents (costs, additional processing step for their separation, large volumina); (c) the lack of control of the particle size during precipitation; and (d) the concentration of adsorbed colourant in the substrate which is too low for some fields of application.

U.S. Pat. No. 5,037,475 describes the preparation of a coloured metallic pigment which is carried out by adsorbing in a first step a carboxylic acid group-carrying polymer to a metal pigment and then, in a second step, adsorbing a coloured organic pigment to the surface of the modified metal pigment obtained in the first step. The disadvantages of this process are (a) the restriction to COOH-group-carrying polymers; (b) the restriction to metallic pigments; (c) that the thickness of the polymer layer between modified metal pigment and organic pigment cannot be controlled; and (d) that the adhesion in some organic pigments does not suffice for commercial applications.

EP-A 278 633 discloses the preparation of coloured mica pigments which is carried out by precipitating a polymer carrying anionic groups with a polyvalent metal cation in the presence of mica and an organic pigment. This process has the disadvantage of affording instead of a pure end product mixtures consisting of coloured mica pigments (mica, organic pigment and precipitated polymer), mica and precipitated polymer, organic pigment and precipitated polymer, and also precipitated polymer. Using this process, it is furthermore impossible to control the layer thickness of the polymer applied by precipitation between mica particles and organic pigment particles.

Accordingly, it is the object of this invention to provide a composite pigment which does not have the above disadvantages. In particular, a process is to be found which does not require a precipitant. In addition, possible aggregation of pigment particles and possible uncontrolled chemical reactions, such as polymerisation, should be prevented. The preparation process should furthermore be simple, the layer thickness of the colourant on the substrate, or on the layer material separating the substrate and the colourant, should be controllable, and the concentration of the colourant in the composite pigment should be sufficiently high. Finally, a process should be provided in which colourants, in particular dyes, can be used without chemical modification, i.e. without binding them covalently to another material.

Accordingly, a composite pigment has been found which consists of a colourant and a substrate, using a substrate (S) and a colourant (C), which are each coated with ions or ionisable compounds having a charge rotating in the same direction, and, if desired, additional ions or ionisable compounds having a charge rotating in the same direction as layer material (L), wherein either (I) the sign of the charge of the coating of S, or the sign of the charge of the coating of S and of the charge of L, which is the same, is opposite to that of the charge of the coating of C, or (II) the sign of the charges of the coatings of S and C is the same and is opposite to that of the sign of the charge of L.

Furthermore, there has been found a process for the preparation of the novel composite pigments, their use for the preparation of pigmented material, in particular for pigmenting high molecular weight organic materials, in particular biopolymers, plastic materials, glasses, ceramic products, for formulations of decorative cosmetics, for the preparation of paint systems, preferably automotive lacquers, printing inks, inks and dispersion paints, as well as pigmented material comprising the novel composite pigments.

The coated substrate and/or coated colourant can also be replaced with an uncoated substrate and/or colourant by coating these in a first step and then preparing the novel composite pigments with the pigment components coated in this manner.

According to this invention, a substrate is used which is coated with at least one compound selected from the group consisting of (a) a polymer carrying ionic or ionisable functional groups, (b) an inorganic polyelectrolyte, (c) a silane, in particular if the modified substrate contains silicium, (d) a phosphonate and/or phosphate ester carrying ionic or ionisable functional groups, in particular if the modified substrate contains aluminium and/or titanium.

Substrates used for the novel composite pigment can be silicates, such as naturally occuring and synthetic mica, e.g. biaxed mica and muscovites, in particular muscovite, phlogopite, biotite, talcum flakes and glass flakes, iron mica, metal pigments consisting of aluminium, zinc, iron, nickel, tin, copper and silver as well as their alloys, preferably aluminium, and mica coated with metal oxide.

The metal pigments can be used in the form of an uncoated or coated powder or paste. As coating materials it is possible to use metal oxides, preferably silicium dioxide or aluminium oxide, in a manner known per se.

The corresponding substrates are commonly known (see e.g. the documents mentioned at the outset) so that further details may be dispensed with here.

A preferred embodiment of this invention uses metal oxide-coated substrates, preferably those based on mica and aluminium. For the metal oxide coating it is suitable to use the customary highly refractive colourless or coloured metal oxides, such as iron(III)oxide, chromium(III)oxide and titanium dioxide, zirconium dioxide and tin dioxide and their mixtures. In this case, the substrates can be coated with only one metal oxide layer or also with several different metal oxide layers.

The preparation of the metal oxide-coated substrates is commonly known.

Metal oxide-coated, preferably titanium dioxide-coated, mica pigments are also commercially available, for example under the registered trademarks Iriodin® (E. Merck, Darmstadt), Flonac® (Kemira Oy, Pori, Finland) and Mearlin® (The Mearl Corporation, New York).

Preferred substrates are those having a particle size in the range from 1 to 500, particularly preferably from 5 to 150 μm. According to findings to date, the monomodal or bimodal distribution of the particle size is not relevant for the success of the invention.

Furthermore, it is preferred to use substrates having an even surface, particularly preferably substrates in platelet form, for example the mica or aluminium flakes mentioned above.

According to this invention, the substrates are coated with ions or ionisable compounds having a charge rotating in the same direction.

For coating the substrates, it is possible to use
organic polymers carrying ionic or ionisable functional groups, for example polyallylamine hydrochloride, polyethylene imine, polydiallyidimethylammonium chloride, poly-N-methyl-4-vinylpyridinium bromide, polylysine hydrobromide, polyacrylic acid, polymethacrylic acid, polyethylenesulfonic acid, polyvinylsulfonic acid, polystyrenesulfonic acid, polyvinylphenyl sulfuric acid (phenolate), maleic acid alkene copolymer, maleic acid vinyl alkyl ether copolymer, polyglutaminic acid, as well as the corresponding copolymers composed of neutral amino acids, polyvinyl amine, polyethylene imine, polyvinyl-4-alkylpyridinium salt, polymethylene-N,N-dimethylpiperidinium salt, polyvinylbenzyltrimethylammonium salt, suitable ionic or ionisable functional groups also being, for example, $(HO)_2P(O)-$, $-CH_2-CHW^1-$, wherein $W^1$ is $-PO_3H_2$, $-SO_3H$, $-OSO_3H$, $-SO_2H$, p-$(MeN(Et)_2-CH_2-)$phenylene, $-COOH$, o-, m-, p-$(HO_3S-)$-phenylene, $-NH_2$, p-pyridyl, $-C(O)-$ O-$(CH_2)_2-NMe_2$; $-CH_2-CH_2-W^2-$, wherein $W^2$ is $-NH-$ or

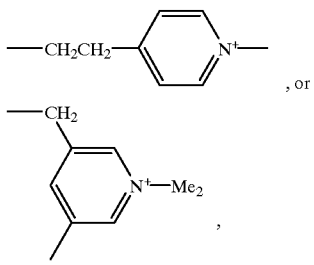

polyallylamine hydrochloride being preferably used; the corresponding compounds are known or can be prepared by known methods, such as those disclosed EP-A 472 990;

inorganic polyelectrolytes, such as zirconium phosphate, basic aluminium salts, such as $Al_{13}O_4(OH)_{12}(H_2O)_{24}Cl_7$, preferably zirconium phosphate and $Al_{13}O_4(OH)_{12}(H_2O)_{24}Cl_7$;

silanes carrying ionic or ionisable groups, in particular if the substrate is based mainly on silicium, for example $$R^1OSi(R^2R^3)-(CH_2)_n-Z \qquad \text{I,}$$

wherein $R^1$ is hydrogen or alkyl, $R^2$ and $R^3$ are each independently of the other alkyl, alkoxy or hydroxy, Z is $-NH_2$, $-P(O)(OH)_2$ or $-N(H)P(O)(OH)_2$, and n is 2, 3, 4, 5, 6, 7 or 8.

$R^1$ is suitably e.g. hydrogen, the alkyl radical $C_1-C_4$alkyl, such as methyl, ethyl, n-, i-propyl, n-, i-, sec- and tert-butyl, preferably hydrogen, methyl and ethyl.

$R^2$ and $R^3$ defined as alkyl radical $C_1-C_4$alkyl may be, for example, methyl, ethyl, n-, i-propyl, n-, i-, sec- and tert-butyl, and defined as alkoxy radical $C_1-C_4$alkoxy e.g. methoxy, ethoxy, n-, i-propoxy, n-, i-, sec- and tert-butoxy. Methyl, ethyl and methoxy and ethoxy are preferred.

Particularly preferred silanes of formula I are $HO(Me)_2Si-(CH_2)_3-P(O)(OH)_2$, 3-aminopropyl-trimethoxysilane, 3-aminopropyltriethoxysilane, 3-aminopropylmethyldiethoxysilane.

Silanes of formula I can either be bought or can be prepared by the method described in Journal of Physical Chemistry, 92(9) (1988), p. 2597 to 2601.

Phosphonates and/or phosphate esters carrying ionic or ionisable groups, in particular if the substrate is based mainly on aluminium or titanium dioxide, for example

| $(HO)_2(O)P-(CH_2)_{m1}-E$ | IIa |
| $(HO)_2(O)P-(CH_2)_{m2}$phenylene-E | IIb |
| $(HO)_2(O)P-(CH_2)_{m3}$bisphenylene-E | IIc | wherein E is $-NH_2$ or $-P(O)(OH)_2$, m1 is a natural number from 4 to 30, and m2 and m3 are 0 or 1.

Phosphonates of formula II can be bought and/or are obtainable by the method described in Journal of Am. Chem. Soc. 115 (1993) 11855 to 11862.

Preferred phosphonates II are those, wherein E is -P(O)(OH)$_2$ and m is 4, 5, 6, 7, 8, 9 or 10.

Particularly preferred phosphonates are, for example, $(HO)_2(O)P-(CH_2)_8-P(O)(OH)_2$, $(HO)_2(O)P-CH_2$bisphenylene-$CH_2-P(O)(OH)_2$, $H_2N$-phenylene-$(CH_2)_r-P(O)(OH)_2$, $H_2N-(CH_2)_{r1}$-bisphenylene-$(CH_2)_{r2}-P(O)(OH)_2$, wherein r, r1 and r2 can be each independently of one another 0 and 1, the phenylene and bisphenylene radicals preferably being substituted in para-position.

In a preferred embodiment of this invention, a substrate is used which is coated at least twice with ions or ionisable compounds having a charge rotating in the same direction, the charges of adjacent layers bearing opposite signs.

In a particularly preferred embodiment of this invention, the substrates coated with silane I, phosphonate II (where E=—P(O)(OH)$_2$) or phosphate ester can, for example, be aftertreated with a di-, tri- or tetravalent metallic cation and with α,ω-bisphosphonate to achieve a more even surface and, if desired, an increase in charge. Depending on the charge on the surface of the coated substrate, the coated substrate is in this case usually reacted either with the α,ω-bisphosphonate, if the substrate is positively charged, or with the polyvalent cation, if the surface of the substrate material is negatively charged. Treatment with α,ω-bisphosphonate results in a substrate having a negative surface which can then be further reacted, if desired, with one of the above-mentioned polyvalent metal cations, in particular if the substrate should be positively charged. Treatment with the cation results in a substrate having a positive surface which can be further reacted, if desired, with the α,ω-bisphosphonate, in particular if the substrate should be negatively charged. In principle, this treatment can be repeated any number of times, for example until a uniformly even surface is obtained. Depending on the substrate used, this may usually be determined by a few preliminary tests.

Di-, tri- or tetravalent metallic cations can be those of zirconium, calcium, zinc, aluminium, titanium, iron and copper, preferably those of zirconium, titanium, aluminium, zinc and calcium. The corresponding cations are preferably used in the form of their water-soluble salts, such as chlorides, oxichlorides or sulfates. Examples to be mentioned are zirconyl dichloride, zirconium sulfate, zirconium ammonium carbonate, zirconium acetate, zirconium propionate, titanium(IV)chloride and titanyl sulfate as well as corresponding chelates with e.g. acetyl-acetonate and triethanolamine.

α,ω-Bisphosphonate may be the phosphonates of formula II, wherein E is —P(O)(OH)$_2$, preferably those containing 8 to 10 carbon atoms, phenylene radicals and bisphenylene radicals. Examples to be mentioned are 1,8-octanediylbis(phosphonic acid), 1,9-nonanediyl-bis(phosphonic acid), 1,10-decanediylbis(phosphonic acid) and (HO)$_2$(O)P-CH$_2$para-bis-phenylene-CH$_2$-P(O)(OH)$_2$.

This preferred aftertreatment is usually carried out according to the method described in J. Phys. Chem. 92 (1988) p. 2597–2601.

In another preferred embodiment of this invention, the substrates modified with a phosphonate or phosphate ester can be reacted with hydrogen or with a metal cation, for example with an alkali metal cation or one of the above-mentioned polyvalent metal cations (variant a). However, it is also possible to react the substrate so obtained, which now has a positive charge, with another phosphonate or phosphate ester of formula II, in particular to obtain a substrate having a negatively charged surface (variant b). It is particularly preferred to react the substrate obtained in variant a with a phosphate and subsequently treating it with hydrogen, with a cation of an alkali metal, such as sodium or potassium, or with an ammonium salt, such as a tetraalkylammonium salt, e.g. tetrabutylammonium salt.

The substrate is usually coated by contacting the components preferably in a solvent, such as water, or in a polar organic solvent, such as alcohols or dimethylformamide, water-soluble organic solvents being preferred, such as methanol, ethanol and tetrahydrofuran, or mixtures thereof, usually in the temperature range from room temperature to 100° C., preferably at atmospheric pressure and then, after sufficient contact time, processing the desired product in a manner known per se, for example by filtering and washing. If desired, customary dispersants may also be used in the coating.

In this process, the coating components are usually added in high excess relative to the amount required for monocoating, excess material preferably being removed by, or during, the above-mentioned filtration.

The preferred substrate is usually titanium-coated mica which is coated first with HO(Me)$_2$Si—(CH$_2$)$_3$—P(O)(OH)$_2$ and then with a compound containing the zirconium cation Zr$^{4+}$ and which is then aftertreated with an inorganic phosphate (e.g. of the Iriodin® type), and also aluminium flakes which are coated first with (HO)$_2$(O)P—(CH$_2$)$_8$—P(O)(OH)$_2$ and then with a compound containing the Zr$^{4+}$ cation and which are then aftertreated with inorganic phosphates (e.g. those of Silberline).

According to this invention a colourant is used which is coated with at least one compound selected from the group consisting of
 (a) a polymer carrying ionic or ionisable functional groups,
 (b) an inorganic polyelectrolyte,
 (c) a silane,
 (d) a phosphonate and/or phosphate ester carrying ionic or ionisable functional groups, and
 (e) with a dye carrying at least one ionic or ionisable functional group.

In principle, the colourants used may be all inorganic and organic pigments as well as dyes, preferably inorganic and organic pigments, particularly preferably organic pigments. Precondition for using (soluble) dyes is that they may be brought into an insoluble form, for example by the choice of a suitable solvent, in which coating is possible.

Typical examples of organic pigments are azo pigments, for example monoazo pigments, diazo pigments, naphthene pigments, benzimidazole pigments, disazo condensation pigments, metal complex pigments, isoindolinone pigments and isoindoline pigments, indigo, quinophthalone pigments, dioxazine pigments and polycyclic pigments, such as quinacridone, phthalocyanine, perylene, perinone and thioindigo pigments, and also anthraquinone pigments, such as aminoanthraquinone, hydroxyanthraquinone, anthrapyrimidine, indanthrone, flavanthrone, pyranthrone, anthanthrone and isoviolanthrone pigments and also diketopyrrolopyrrole ("DPP") pigments, preferably anthraquinone, DPP, azoquinacridone, phthalocyanine and perylene pigments, particularly preferably DPP, azoquinacridone, phthalocyanine and perylene pigments.

It is also possible to use metal oxide-coated pigments which are described in detail, inter alia, in EP-A 296 111 and in the state of the art discussed therein.

Pigments having a particle size in the range from 10 nm to 1 μm are normally used.

The cited colourants are commonly known and many are commercially available. The coating of the colourants is usually carried out in general analogy to the application of the coating agents to the substrates.

In a preferred embodiment of this invention, the dyes carrying at least one ionic or ionisable functional group can also be DPP or phthalocyanine compounds which are substituted by at least one sulfonic acid group or by at least one amino group and which are therefore soluble.

Preferred coated colourants are pigments coated with zirconium phosphate, with a titanium, tin or zirconium chelate complex, such as zirconium acetylacetonate, which pigments, if desired, are coated with an acrylic resin, typically prepared by polymerisation of dimethylaminoethyl methacrylate or by its copolymerisation with methacrylic acid. As particularly preferred pigments it is possible to use 1,4-diketo-2,5-dihydropyrrolo-[3,4-c]pyrroles which, if desired, are substituted at the N atoms and/or in 3- and 6-position. Corresponding pigment compositions are described in detail, inter alia, in EP-A 656 403 and EP-A 656 402 so that further details may be dispensed with here.

The weight ratio of coated substrate to coated colourant is usually chosen from the range of 1:1 to 200:1, preferably of 1:1 to 70:1.

In step a of another embodiment of this invention, the composite pigments are prepared by contacting a substrate (S) and a colourant (C), which are each coated with ions or ionisable compounds having a charge rotating in the same direction, the charge of the coating of S and the charge of the coating of C bearing different signs.

This is conveniently done by contacting the components at a temperature in the range from generally 0 to 100, preferably from 15 to 45° C., at atmospheric pressure and at a pH in the range from usually 5 to 9, in a solvent, preferably in water, $C_1$–$C_4$alkanols, e.g. methanol, ethanol, n-, i-propanol or n-butanol and their mixtures with each other or with water, at a weight ratio of solvent to substrate in the range from usually 0.1 to 95, preferably from 1 to 50% by weight, based on the substrate. The residence time, depending on the chosen temperature, is usually chosen from the range of 0.1 to 20 h. Prior to the addition of the dispersant, customary dispersants may, if desired, be added to the reaction mixture in amounts usually ranging from 0.1 to 25% by weight, based on the reaction mixture.

In preferred embodiment of this invention, titanium dioxide-coated mica pigments are first dispersed with a silane I, wherein Z is the radical —$P(O)(OH)_2$, preferably with HO—$SiMe_2$—$(CH_2)_3$—$P(O)(OH)_2$, and are then after-treated first with $Zr^{4+}$, then with an inorganic phosphate, subsequently adding a polyallylamine hydrochloride solution, usually at room temperature, so that the substrate has a positively charged surface. The pH is particularly preferably adjusted to the range of 6.5 to 7.5, more preferably of 6.8 to 7.2, with a customary buffer such as tetrabutylammonium hydroxide ("TBAOH"). After coating, which is usually complete after halt an hour to two hours, preferably after one hour, the coated substrate so obtained is filtered and washed. A coated colourant having a negatively charged surface is then usually added to the aqueous dispersion of the coated substrate, preferably 1,4-diketo-2,5-dihydropyrrolo-[3,4-c]pyrroles ("DPP") coated with zirconium phosphate and, if desired, substituted in 3- and 6-position by alkyl or aryl. It is particularly preferred to add insoluble coated colourants in the form of a dispersion, preferably in the presence of a customary neutral dispersant such as polyvinyl alcohol. The composite pigment obtained in this manner can be processed as usual, e.g. by filtration and washing, and can then be further utilised.

In another embodiment of this invention, the composite pigments are prepared by contacting the composite pigment obtained in step (a) with a layer material (L), L denoting additional ions or ionisable compounds having a charge rotating in the same direction, the charge of S bearing the opposite sign to the charge of the coating of the colourant used in (a), and, if desired, (c) applying an additional coated colourant to the composite pigment obtained in step (b) in the manner described above and, if desired, (d) repeating steps (b) and (c) any number of times.

In another preferrred embodiment of this invention, the novel composite pigments are prepared by contacting (a) a substrate (S), which is coated with ions or ionisable compounds having a charge rotating in the same direction, and a layer material (L), consisting of ions or ionisable compounds having a charge rotating in the same direction, the charge of the coating of S and the charge of L bearing opposite signs, and then adding a colourant (C) which is coated with ions or ionisable compounds having a charge rotating in the same direction, the charge of C bearing the opposite sign to that of the charge of L, and, if desired, (b) applying another layer material to the composite pigment obtained in step (a) and, if desired, (c) repeating the application of C and L any number of times.

It is thus possible to prepare composite pigments having, for example, layers arranged in the order of S//C, S//C//L, S//C//L//C . . . , S//L//C, S//L//C//L etc.

In a particularly preferred embodiment of this invention for the preparation of the novel composite pigments, the layer thickness of the layer material is chosen such that the layer material is in each case applied as a very thin layer, preferably as monolayer, i.e. the layer thickness in this case corresponds to the thickness of a single layer. The layer material is usually used in excess and the non-adsorbed amount is in each case preferably removed by filtration. It is preferred to deposit 1 to 5 C//L layer pairs, preferably 1 to 3.

In another preferred embodiment of this invention, the coated substrate and/or coated colourant is replaced with an uncoated substrate and/or colourant which is then coated and the composite pigments are then prepared as described above.

Another preferred embodiment of this invention relates to the preparation of the pigments, which are composed of a substrate, a colourant and a layer material, by mixing a dispersion of the coated colourant and a dispersion of the coated substrate and of the layer material. The dispersion medium is preferably a polar solvent such as water, $C_1$–$C_4$alkanols, such as methanol, ethanol, n-, i-propanol or n-butanol, and their mixtures. The concentration of the substrate or colourant in the respective dispersion is usually chosen from the range of 0.1 to 50% by weight, based on the dispersion medium. The amount of coated colourant to coated substrate is usually chosen in a ratio ranging from 0.01:1 to 2:1, preferably from 0.01:1 to 0.8:1. The ratio of layer material to coated substrate is usually chosen such that the layer material provides enough charge carriers to apply another layer consisting of coated colourant having a charge opposite to that of the layer material. The reaction temperature is usually chosen from the range of 15 to 80° C., preferably of 15 to 50° C. Depending essentially on the chosen temperature, the reaction time is usually chosen from the range of 0.5 to 12 hours.

The layer material is preferably at least one compound selected from the group consisting of (a) organic polymers carrying ionic or ionisable functional groups, (b) inorganic polymers carrying ionic or ionisable functional groups, (c) monomeric substances of formula III $$\text{ion-}Z^1\text{—}(\text{—}Y^1\text{—}Z^2\text{—})_{p1}\text{—}X\text{—}Z^3\text{—}Y^2\text{—}Z^4\text{—ion} \qquad \text{III}$$

wherein X is preferably one of the following groups

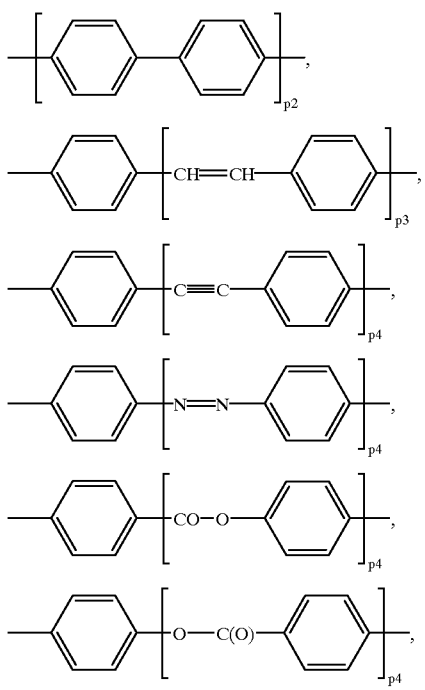

the aromatic nuclei in which groups can be mono- to trisubstituted by methyl, fluoro or chloro, or can be hydrated to cyclohexane, $Y^1$ and $Y^2$ are each independently of the other —($CH_2$—)$_t$—, —(—$SiMe_2$—O—)$_t$—, —(CH=CH—)$_t$— or —(—C≡C—)$_t$—, the hydrogen atoms in which groups can be partially or completely substituted by methyl, fluoro or chloro, $Z^1$, $Z^2$, $Z^3$ and $Z^4$ are each independently of one another a single bond, —O—, —S—, —CO—, —SO—, —$SO_2$—, —CO—O—, —O—CO—, =N—CO, —CO—N=, —NH— or —N($C_1$-$C_4$alkyl)—, ion is a cation, an anion, or a group which can be ionised to the cation or anion, p1 is 0 or 1, preferably 1, p2 is 0, 1, 2, 3, 4, 5, 6 or 7, p3 is 1, 2 or 3, p4 is 1 or 2, and t is an integer from 1 to 20, the charges of the ionic or ionisable groups bearing the same sign.

Suitable anionic or cationic or ionisable groups in organic polymers are, for example, those which have already been mentioned above for the organic polymers as coating material for the substrate.

Illustrative examples of polyelectrolytes are: polyacrylic acid, polymethacrylic acid, polyethylenesulfonic acid, polyvinylsulfonic acid, polystyrenesulfonic acid, polyvinylphenylsulfuric acid (phenolate), maleic acid alkene copolymer, maleic acid vinyl alkyl ether copolymer, polyglutaminic acid, polylysine, as well as the corresponding copolymers composed of neutral amino acids, polyvinyl amine, polyethylene imine, polyvinyl-4-alkylpyridinium salt, polymethylene-N,N-dimethylpiperidinium salt, polyvinylbenzyltrimethylammonium salt. Particularly preferred polyelectrolytes are polymers having the repeating units —$CH_2$—CH$W^1$—, wherein $W^1$ is —$OSO_3$H, p-(MeN(Et)$_2$—$CH_2$—)phenylene, o-, m-, p-($HO_3$-S-)phenylene,

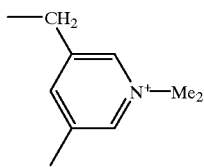

and —CH[($CH_2$)$_4$—$NH_2$]—C(O)N(H)— as well as dextransulfate, heparin or polyallylamine.

The polymeric organic material chain for the layer material can thus be a polyolefin, an acrylic polymer, a polyvinyl acetate, a polyester, a polyamide, a poly- or copolyamino acid, such as polylysine or polyglutaminic acid, a ionic polysaccharide or another polymer known to the skilled person. The polymer can carry the ions or the ionisable functional groups in the monomer unit and can thus be water-soluble, or it may also be at first a hydrophobic, and thus water-insoluble, polymer into which the ions or ionisable groups are incorporated by polymer-analogous reactions.

Inorganic polymers carrying ionic or ionisable functional groups having the same charge are preferably inorganic polymers based on metal ions and oxygen, hydroxyl groups, phosphates or phosphonates.

The particle size of the inorganic polymers is usually chosen from the range of $3 \times 10^{-3}$ μm to 10 μm.

Illustrative examples of inorganic polymers are:

inorganic solids arranged in layers, for example $M_xMoO_3$, $M_xFeOCl$, $M_xMX_2$, wherein Mx is hydrogen, lithium or sodium, M is niobium, molybdenum, tungsten or rhenium, and X is sulfur, selenium or tellurium, vermiculite, $Zr(HPO_4)_2 \cdot H_2O$, $HCa_2Nb_3O_{10}$, $HTiNbO_5$, mica, montmorillonite, hectorite, saponite, nontronite, biedellite, hydrotalcite and $Zr(O_3PR)_2$, wherein R is a substituted organic alkyl or aryl radical, e.g. $C_1$–$C_4$alkyl, preferably methyl, ethyl, n-, i-propyl, n-, i-, sec-, tert-butyl, or phenyl, containing a —$NH_2$, —COOH or —$SO_3$H group, for example 3-aminopropylphosphonic acid, 2-carboxyethylphosphonic acid. The cited compounds are known, inter alia, from Materials Science Forum Vol. 152–153 (1994) p. 1–12 and/or are commercially available.

Colloids based on aluminium oxide. e.g. boehmite, or based on silicium oxide, e.g. Ludox® (DuPont) or Bindzil®330/220 (Eka Nobel).

Oligomeric ions, preferably highly charged ones such as $[Al_{13}O_4(OH)_{24}]^{7+}$, $[Zr(OH)_{16x}]^{x+}$, chlorohydrol (commercially available e.g. under the registered trademark Locron®L, of Hoechst, or Bindizil®CAT, of Eka Nobel), oxides of vanadium, molybdenum and tungsten such as vanadates, typically $V_{10}O_{28}^{6-}$, and isopoly acids and heteropoly acids and their salts, such as $Mo_7O_{24}^{6-}$ or $PV_3W_9O_{40}^{6-}$ (described, inter alia, in Advanced Inorganic Chemistry, Ed. Cotton and Wilkinson, Wiley, Interscience, 1980, 4the Ed. p. 712–714 (vanadates), 852–861 molybdenum oxides and tungsten oxides).

The layer material preferably consists of polyallylamine hydrochloride, $Zr(HPO_4)_2 \cdot H_2O$, hectorite, synthetic hectorite, $[Al_{13}O_4(OH)_{24}]Cl_7$, boehmite, silicates and chlorohydrol (Locron®L).

A preferred embodiment of this invention relates to a composite pigment consisting of titanium-coated mica (Iriodin®), which is coated by the process described above with a silane of formula I, then with $Zr^{4+}$ and then with an inorganic phosphate. The mica coated in this manner is then coated with polyallyamine hydrochloride or aluminium sol $(Al_{13}O_4(OH)_{24}Cl_7)$ or boehmite. The substrate so prepared is then contacted with coated pigment and the composite pigment thus obtained is then coated with a layer consisting of polyallylamine hydrochloride or aluminium sol, another layer consisting of coated pigment being subsequently added, it desired.

Another preferred embodiment of this invention relates to composite pigments where the substrate consists of coated aluminium flakes (for example Sparkle Silver Premier Grade type, of Silberline, which is coated first with e.g. $(HO)_2P(O)—(CH_2)_8—P(O)(OH)_2$, then with $Zr^{4+}$ and finally with an inorganic phosphate). If desired, the charge of the surface of the substrate can be reversed, preferably with polyallylamine hydrochloride, resulting in a positively charged surface. The coated colourant consists particularly preferably of pigments coated with zirconium phosphate, the surface of the substrate then needing to be negatively charged, for example as described above, if the last layer is an inorganic phosphate.

Particularly preferred composite pigments are $TiO_2$-coated mica comprising as first layer $HO(Me)_2Si—(CH_2)_3—P(O)(OH)_2$. Additional layers with the following compounds are applied to this first layer in the indicated order: zirconyl chloride (as $Zr^{4+}$ supplier), which is subsequently treated with phosphoric acid; polyallylamine and a diketopyrrolopyrrole as colourant.

Other particularly preferred composite pigments are $TiO_2$-coated mica comprising as first layer $HO(Me)_2Si—(CH_2)_3—P(O)(OH)_2$. Additional layers with polyallylamine and a diketopyrrolopyrrole colourant are applied to this first layer in the indicated order.

The composite pigments prepared according to this invention can be advantageously used for many purposes, such as for the preparation of pigmented material, preferably for pigmenting high molecular weight organic materials, such as biopolymers, plastic materials, including fibres, glasses, ceramic products, for formulations of decorative cosmetics, for the preparation of inks, printing inks, paint systems, preferably automotive lacquers, and dispersion paints.

Illustrative examples of suitable high molecular weight organic materials which can be coloured with the novel compounds are vinyl polymers, such as polystyrene, poly-α-methyl-styrene, poly-p-methylstyrene, poly-p-hydroxystyrene, poly-p-hydroxyphenylstyrene, poly-methyl methacrylate and polyacrylamide as well as the corresponding methacrylic compounds, polymethylmaleate, polyacrylonitrile, polymethacrylonitrile, polyvinyl chloride, polyvinyl fluoride, polyvinylidene chloride, polyvinylidene fluoride, polyvinyl acetate, polymethyl vinyl ether and polybutyl vinyl ether; polymers derived from maleinimide and/or maleic anhydride, such as copolymers of maleic anhydride with styrene; polyvinyl pyrrolidone; ABS; ASA; polyamides; polyimides; polyamidimides; polysulfones; polyether sulfones; polyphenylene oxides; polyurethanes; polyureas; polycarbonates; polyarylenes; polyarylenesulfides; polyepoxides; polyolefins, such as polyethylene and polypropylene; polyalkadienes; biopolymers and their derivatives, such as cellulose, cellulose ethers and cellulose esters, such as ethyl cellulose, nitrocellulose, cellulose acetate and cellulose butyrate, starch, chitin, chitosan, gelatine, zein; natural resins; synthetic resins, for example alkyd resins, acrylic resins, phenolic resins, epoxy resins, aminoformaldehyde resins, such as urea/formaldehyde and melamine/formaldehyde resins; rubber; casein; silicone and silicone resins; caoutchouc, chlorinated rubber; and also polymers which are used, for example, as binders in paint systems, such as novolaks derived from $C_1$–$C_6$ aldehydes, e.g. formaldehyde and acetaldehyde and a binuclear or mononuclear, preferably mononuclear, phenol which, if desired, may be substituted by one or two $C_1$–$C_9$alkyl groups, one or two halogen atoms or a phenyl ring, such as o-, m- or p-cresol, xylene, p-tert-butylphenol, o-, m- or p-nonylphenol, p-chlorophenol or p-phenylphenol, or from a compound containing more than one phenolic group, typically resorcinol, bis(4-hydroxyphenyl)methane or 2,2-bis(4-hydroxyphenyl)propane; as well as suitable mixtures of the cited materials.

Particularly preferred high molecular weight organic materials, in particular for the preparation of a paint system, printing ink or ink, are, for example, cellulose ethers and esters, such as ethylcellulose, nitrocellulose, cellulose acetate and cellulose butyrate, natural resins or synthetic resins (polymerisation or condensation resins), for example aminoplasts, in particular urea/formaldehyde resins and melamine/formaldehyde resins, alkyd resins, phenolic plastics, polycarbonates, polyolefins, polystyrene, polyvinyl chloride, polyamides, polyurethanes, polyesters, ABS, ASA, polyphenylene oxide, rubber, casein, silicone and silicone resins as well as their possible mixture with each other.

It is also possible to use high molecular weight organic materials in dissolved form as film formers, for example boiled linseed oil, nitrocellulose, alkyd resins, phenolic resins, melamine/formaldehyde and urea/formaldehyde resins and acrylic resins.

The cited high molecular weight organic compounds can be obtained singly or in mixtures, for example as granulate, plastics, melts or in the form of solutions, in particular for the preparation of spinning solutions, paint systems, coatings, inks or printing inks.

In a particularly preferred embodiment of this invention, the novel composite pigments are used for mass colouring polyvinyl chloride, polyamides and, in particular, polyolefins such as polyethylene and polypropylene, and for the preparation of paint systems, including powder coatings, inks, printing inks and coating compounds.

Examples of preferred binders for paint systems to be mentioned are alkyd/melamine surface coating resins, acryl/melamine surface coating resins, cellulose acetate/cellulose butyrate paints and two-component paints based on polyisocyanate of crosslinkable acrylic resins.

According to findings so far, the novel composite pigments can be added to the material to be coloured in any desired amount depending on the end use requirements. In the case of high molecular weight organic materials, for example, the novel composite pigments can be used in amounts in the range from 0.2 to 40, preferably from 0.5 to 20 % by weight, based on the total weight of the pigmented high molecular weight organic material.

The high molecular weight organic materials are normally coloured with the novel composite pigments such that said composite pigments, if desired in the form of masterbatches, are admixed to the high molecular weight organic materials using customary suitable appliances, for example roll mills, mixing or grinding apparatus. The pigmented material is then usually brought into the desired final form by methods known per se, such as calendering, moulding, extruding, coating, casting or injection moulding.

To produce non-brittle mouldings or to reduce their brittleness, so-called plasticisers may be added to the high molecular weight substances prior to moulding. These plasticisers may be, for example: the esters of phosphoric acid, phthalic acid and sebacic acid. The plasticisers can be added before, during or after colouring the high molecular substances with the novel composite pigments.

To obtain different shades, the novel composite pigments can be advantageously added in admixture with fillers, transparent and opaque white, coloured and/or black pigments and conventional luster pigments in the desired amount.

To prepare paint systems, coating compositions, inks and printing inks, the corresponding high molecular weight organic substances, such as binders, synthetic resin dispersions and the like, and the novel composite pigments, are usually dispersed or dissolved, if desired together with customary additives, such as fillers, paint auxiliaries, siccatives, plasticisers and/or additional pigments, in a shared solvent or solvent mixture. This may be effected by dispersing or dissolving the individual components by themselves or also several together and only then bringing all components together, or by adding all of them in one go. For printing applications, all conventional industrial printing methods may be used, such as screen printing, rotogravure, bronze printing, flexographic printing and offset printing.

The composite pigments prepared according to this invention have the advantage that they can be prepared by a process which does not require a precipitant. In addition, the novel process precludes possible aggregation of pigment particles as well as possible uncontrolled chemical reactions such a polymerisation. Furthermore, the novel method of preparation is simple, the layer thickness of the pigment on the substrate or on the adhesion promoter can be controlled and the concentration of the colourant in the composite pigment is sufficiently high. Finally, a process is provided in which colourants, in particular dyes, can be used without chemical modification, i.e. without any covalent bonding to another material.

EXAMPLES

A Preparation of coated substrate
A1 Preparation of the coating material

Example 1

In general analogy to the instructions of Journal of Physical Chemistry, 92(9) 1988), p. 2597–2601, 20 g of 1,3-bis(3-chloropropyl)-1,1,3,3-tetramethyldisiloxane are reacted with 116.5 g of triethyl phosphite at 160° C. over 5 hours. Excess triethyl phosphite is then removed by distillation at reduced pressure. Subsequently, 70 ml of conc. hydrochloric acid are added to the reaction mixture. Affther heating this reaction mixture for 8 hours to 100° C., it is cooled to room temperature and diluted with methanol until said reaction mixture, which comprises $HO(Me)_2Si—(CH_2)_3—P(O)(OH)_2$, has a volume of 500 ml.

Example 2

In general analogy to the instructions of J. Am. Chem. Soc. 115 (1993) 11855–11862, 5.44 g of α,ω-dibromooctane are reacted with 8.3 g of triethyl phosphite at 150° C. for 6 hours. After cooling this reaction mixture, 30 ml of conc. hydrochloric acid are added. The reaction mixture is heated overnight to 100° C. and is then cooled to room temperature. 10 ml of water are then added to the reaction mixture and the aqueous phase is separated. After removing the water from the separated aqueous phase at reduced pressure, the white solid obtained (consisting of the bisphosphonate $(HO)_2(O)P—(CH_2)_8—P(O)(OH)_2$) is washed with acetonitrile and dried at reduced pressure.

A2 Preparation of the coated substrate

Example 3

A mixture consisting of 50 ml of the solution prepared in Example 1, 3 l of methanol and 120 g of titanium dioxide-coated mica (Iriodin®9221 Rutil Feinblau, of Merck, Darmstadt) is heated for 3 days to 60° C. The solid components are then collected by filtration, washed with water and dispersed in a solution consisting of 12 g of zirconyl chloride in 2 l of water. This suspension is stirred for 2 days at room temperature. The solid is then collected by filtration and washed with water. Subsequently, 1.2 l of 10 % by weight phosphoric acid are added to the washed solid and stirred for two hours. The solid is then collected by filtration, washed, dispersed in 1 l of water and the pH is adjusted to 8.5 with a 0.5 molar aqueous solution of tetrabutylammonium hydroxide. Subsequent filtration affords the coated substrate.

Example 4

The procedure of Example 3 is repeated, but using Iriodin®211.

Example 5

The procedure of Example 3 is repeated, but using Iriodin®231.

Example 6

5 g of titanium dioxide-coated mica (Iriodin®Gold, of Merck, Darmstadt) are treated with a 1% by vol solution of (3-aminopropyl)trimethoxysilane in boiling anhydrous n-octane for 24 h. Subsequent filtration affords the coated substrate.

B Preparation of modified colourant

Example 7

2.8 g of disodium hydrogen phosphate, dissolved in 50 ml of water, are slowly added over 2.5 hours to a mixture consisting of 28.8 g of 1,4-diketo-2,5-dihydro-3,6-diphenyl-pyrrolo[3,4-c]pyrrole (preparation described in EP-A 717, 086) of formula

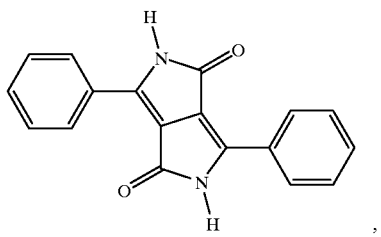

, 5 g of zirconium(IV)acetylacetonate and 250 ml of water. This suspension is then filtered and the residue, which consists of coated colourant, is washed with water and then dried at 80° C.

Example 8

1.1 g of disodium hydrogen phosphate, dissolved in 50 ml of water, are slowly added over 1 hour to a mixture consisting of 26.3 g of 1,4-diketo-2,5-dihydro-3,6-bis(biphenyl-4-yl)-pyrrolo[3,4-c]pyrrole (preparation described in U.S. Pat. No. 4,579,949) of formula

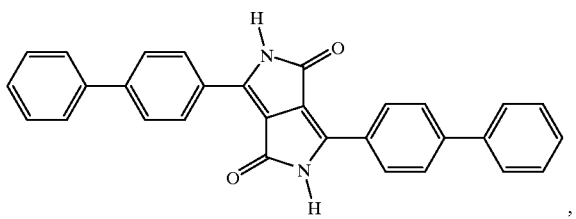

1.7 g of zirconium(IV)acetylacetonate and 400 ml of water. This suspension is then filtered and stored as press cake having a 63.3% by weight solid component consisting of coated colourant.

C. Preparation of composite pigments

Example 9

1 g of titanium dioxide-coated mica (IRIODIN®231) are dispersed in 200 ml of a 0.01 molar aqueous solution of polyallylamine hydrochloride ($M_W$ 50.000 to 65.000 g/mol). The pH is adjusted to 7 with tetrabutylammonium hydroxide. After stirring this suspension for 1 hour at room temperature, it is filtered and the solid residue is washed with water. The press cake so obtained is dispersed in 200 ml of water. A dispersion consisting of 0.05 g of the coated colourant of Example 7 and 10% by weight of polyvinyl alcohol ($M_W$ 22.000 g/mol) is then added to this dispersion and stirred for 8 hours. After filtration, the coloured micaceous pigment is dried for 12 hours at 80° C.

Examples 10 to 20

The procedure of Example 9 is repeated, but using different substrates, colourants. The following Table lists the substances used.

Table: Examples 10 to 20

| Example | Substrate (1 g each) | Colourant | Amount of colourant [g] |
|---|---|---|---|
| 9  | of Example 3 | of Example 7 | 0.05 |
| 10 | of Example 3 | of Example 7 | 0.15 |
| 11 | of Example 3 | of Example 8 | 0.05[1] |
| 12 | of Example 3 | of Example 8 | 0.15[1] |
| 13 | of Example 4 | of Example 7 | 0.05 |
| 14 | of Example 4 | of Example 7 | 0.15 |
| 15 | of Example 4 | of Example 8 | 0.05[1] |
| 16 | of Example 4 | of Example 8 | 0.15[1] |
| 17 | of Example 5 | of Example 7 | 0.05 |
| 18 | of Example 5 | of Example 7 | 0.15 |
| 19 | of Example 5 | of Example 8 | 0.05[1] |
| 20 | of Example 5 | of Example 8 | 0.15[1] |

[1] dried colourant (at 80° C., 12 h)

Example 21

A dispersion consisting of 0.05 g of the coated colourant of Example 7 and 0.005 g of polyvinyl alcohol (as in Ex. 9) is added to 1 g of the coated substrate of Example 6 in 100 ml of water of pH 7 (adjusted with a 0.5 molar TBAOH solution) and this mixture is then reacted for 8 hours. After filtration, the coloured micaceous pigment so obtained is dried for 12 h at 80° C.

Example 22

1 g of the substrate prepared according to Example 3 is dispersed in 200 ml of a 0.01 molar aqueous $Al_{13}O_4(OH)_{12}(H_2O)_{24}Cl_7$ solution. The pH is adjusted to 7 with a 0.5 molar aqueous tetrabutylammonium hydroxide solution. The suspension so obtained is stirred for 1 h at room temperature and is then filtered and the filter residue is washed. After dispersing the press cake so obtained in 200 ml of water, a dispersion consisting of 0.15 g of the colourant prepared according to Example 8 and 0.01 g of polyvinyl alcohol (as in Ex. 9) is added and this mixture is then reacted for 8 hours. After filtration, the coloured micaceous pigment obtained is dried for 12 h at 80° C.

Example 23

0.3 g of the diphosphane prepared according to Example 2, dissolved in 100 ml of ethanol, is added to a suspension consisting of 20 g of an aluminium paste (Sparkle Silver Premier Grade 516AR®, of Silberline) in 20 g of 2-methoxybutanol. After stirring this mixture for 2 hours, the solid is collected by filtration and washed in ethanol. The washed solid and 0.25 g of Zr(acetylacetonate)$_4$ are then dispersed in 100 ml of ethanol and stirred overnight. The solid is then collected by filtration, washed with ethanol, and then 3.3 g of the solid washed in this manner are dispersed in 50 g of ethanol. Subsequently, 100 g of a 0.1 molar solution consisting of $Na_2HPO_4$ are added to this suspension which is then stirred for 1 hour at room temperature. The solid is then collected by filtration and washed with water. The aluminium paste suspension so obtained is then added to 200 ml of water and the pH is adjusted to 8.5 with a 0.5 molar solution of tetrabutylammonium hydroxide. Subsequent filtration affords the aluminium-based coated substrate.

Example 24

3.3 g of the coated substrate prepared according to Example 23 and 0.15 g of polyallylamine hydrochloride ($M_W$ 50.000 to 65000, product of Aldrich) are dispersed in 200 ml of water. The pH is then adjusted to 7 with a 0.5 molar aqueous tetrabutylammonium hydroxide solution. This suspension is stirred at room temperature for 30 min and the solid is then collected by filtration and washed with water. After suspending the press cake so obtained in 200 ml of water, a suspension consisting of 0.15 g of the colourant prepared according to Example 7 in 200 ml of an ethanol/water mixture (volume ratio 1:1) is slowly added. After 8 hours, the solid obtained is collected by filtration and the resulting coloured aluminium flakes are stored as ethanol-containing press cakes.

Example 25

The procedure of Example 24 is repeated, but carrying out the coating with polyallylamine hydrochloride and with the colourant a second time before storing.

Example 26

The procedure of Example 25 is repeated, but carrying out the coating with polyallylamine hydrochloride and with the colourant one more time before storing.

Example 27

The pH of a mixture consisting of 100 ml of ethanol and 3 ml of the solution prepared according to Example 1 is adjusted to 6.5 with a 0.5 molar solution of tetrabutylammonium hydroxide. 10 g of an aluminium treated with tetraethoxysilane (TEOS) (obtained in a manner known per se by hydrolysing TEOS in the presence of the aluminium flakes, the aluminium flakes having an average particle size of 15 μm) are added to this solution and the pH is adjusted to 6 with dilute hydrochloric acid. After heating this suspension for 48 h to 70° C. and then cooling it, the solid component is collected by filtration and the press cake so obtained is washed with ethanol.

A dispersion consisting of 2 g of the press cake so obtained, 0.25 g of Zr(acetylacetonate)$_4$ and 100 ml of ethanol is stirred overnight. The solid component is then collected by filtration, washed with 200 ml of ethanol and added to 200 ml of a 0.1 molar solution of disodium hydrogen phosphate. The resultant dispersion is stirred for 20 min and the solid component is then collected by filtration and the press cake so obtained is washed with water. The press cake is then added to 200 ml of water and the pH is adjusted to 8.5 with a 0.5 molar solution of tetrabutylammonium hydroxide. Filtration affords a coated aluminium substrate.

Example 28

The procedure of Example 24 is repeated, but using the coated aluminium substrate of Example 27.

Example 29

The procedure of Example 25 is repeated, but using the coated aluminium substrate of Example 27.

What is claimed is:

1. A composite pigment comprising a substrate (S) and a colorant (C), wherein the substrate (S) and the colorant (C) are each coated with ions or ionizable compounds having either a positive charge or a negative charge and, optionally, further coated with ions or ionizable compounds, as layer material (L), having either a positive charge or a negative charge and wherein either:

(I) the charge of the coating of S is opposite to the charge of the coating of C and if layer material (L) is present then the charge of the coating of S and the charge of layer material (L) are the same; or (II) where the charge of the coating of S and the charge of the coating of C are the same and layer material (L) is present then the charge of the coating of S and the charge of the coating of C are opposite to the charge of layer material (L) and;

wherein the colorant (C) is an organic pigment selected from the group consisting of azo pigments, naphthene pigments, benzimidazole pigments, disazo condensation pigments, metal complex pigments, isoindolinone pigments, isoindoline pigments, indigo, quinophthalone pigments, dioxazine pigments, polycyclic pigments, phthalocyanine, perylene, perinone pigments, thioindigo pigments, anthraquinone pigments, anthrapyrimidine, indanthrone, flavanthrone, pyranthrone, anthanthrone, isoviolanthrone pigments and diketopyrrolopyrrole (DPP) pigments.

2. A composite pigment according to claim 1, wherein the substrate is coated with at least one ion or ionizable compound selected from the group consisting of (a) a polymer carrying ionic or ionisable functional groups,
(b) an inorganic polyelectrolyte,
(c) a silane,
(d) a phosphonate or phosphate ester carrying ionic or ionisable functional groups, and mixtures thereof.

3. A composite pigment according to either claim 1 or claim 2, wherein the colourant is coated with at least one ion or ionizable compound selected from the group consisting of (a) a polymer carrying ionic or ionisable functional groups,
(b) an inorganic polyelectrolyte,
(c) a silane,
(d) a phosphonate or phosphate ester carrying ionic or ionisable functional groups, and mixtures thereof, and
(e) with a dye carrying at least one ionic or ionisable functional group.

4. A composite pigment according to claim 1, comprising the layer material wherein the layer material consists of at least one compound selected from the group consisting of (a) organic polymers carrying ionic or ionisable functional groups,
(b) inorganic polymers carrying ionic or ionisable functional groups, and
(c) monomeric substances of formula III

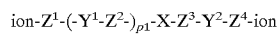

wherein X is preferably one of the following groups

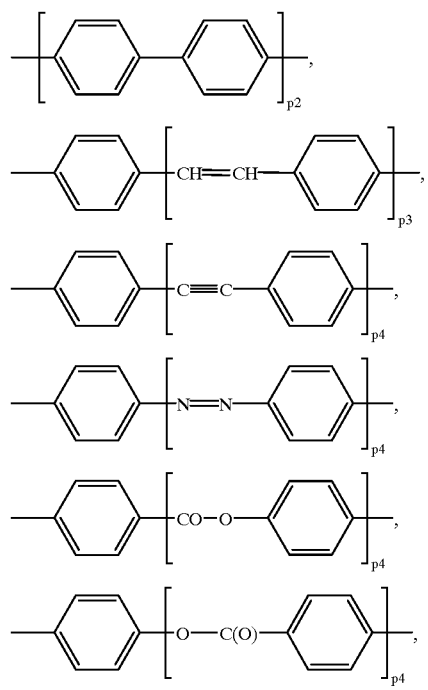

the aromatic nuclei in which groups can be mono- to trisubstituted by methyl, fluoro or chloro, or can be hydrated to cyclohexane, $Y^1$ and $Y^2$ are each independently of the other —(CH$_2$—)$_r$—, —(—SiMe$_2$—O—)$_r$—, —(CH=CH—)$_r$— or —(—C≡C—)$_r$—, the hydrogen atoms in which groups can be partially or completely substituted by methyl, fluoro or chloro, $Z^1$, $Z^2$, $Z^3$ and $Z^4$ are each independently of one another a single bond, —O—, —S—, —CO—, —SO—, —SO$_2$—, —CO—O—, —O—CO—, =N—CO, —CO—N=, —NH— or —N(C$_1$–C$_4$alkyl)-, ion is a cation, an anion, or a group which can be ionised to the cation or anion, p1 is 0 or 1, preferably 1,
p2 is 0, 1, 2, 3, 4, 5, 6 or 7,
p3 is 1, 2 or 3, p4 is 1 or 2, and t is an integer from 1 to 20, the charges of the ionic or ionisable groups bearing the same sign.

5. A composite pigment according to claim 1, wherein the substrate is coated at least twice with ions or ionisable compounds having either a positive or negative charge, the charges of adjacent layers bearing opposite signs.

6. A process, for the preparation of the composite pigment according to claim 1, comprising:
- (a) contacting substrate (S) and colorant (C) wherein the substrate (S) and the colorant (C) are each coated with ions of ionizable compounds having either a positive charge or a negative charge and wherein the charge of the coating of S and the charge of the coating of C bear opposite signs and optionally,
- (b) contacting the composite pigment obtained in step (a) with additional ions or ionizable compounds, as layer material (L), wherein the charge of layer material (L) is opposite the charge of the coating of the colorant (C) and optionally,
- (c) contacting another coated colorant to the composite pigment obtained in step (b), and optionally,
- (d) repeating steps (b) and (c) any number of times.

7. A process, for the preparation of the composite pigment according to claim 1, comprising:
- (a) contacting substrate (S), which is coated with ions of ionizable compounds having either a positive charge or a negative charge, and a layer material (L) consisting of ions or ionizable compounds having either a positive charge or a negative charge, wherein the charge of the coating of S is opposite the charge of layer material (L) and subsequently adding the colorant (C) coated with ions or ionizable compounds having either a positive charge or a negative charge and wherein the charge of the coating of C is opposite the charge of layer material (L) and optionally,
- (b) repeating the application of layer material (L) and the colorant (C) any number of times.

8. A process according to claim 6, which comprises replacing the coated substrate and/or the coated colorant with an uncoated substrate and/or colorant, coating these and subsequently preparing the composite pigments.

9. A process according to claim 7, which comprises replacing the coated substrate and/or the coated colorant with an uncoated substrate and/or colorant, coating these and subsequently preparing the composite pigments.

10. A composite pigment according to claim 1 wherein the organic pigment is selected from the group consisting of monoazo pigments, diazo pigments and quinacridone pigments.

11. A composite pigment according to claim 1, wherein the organic pigment is selected from the group consisting of anthraquinone, DPP, azoquinacridone, phthalocyanine and perylene pigments.

12. A composite pigment according to claim 1, wherein the organic pigment is selected from the group consisting of DPP, azoquinacridone, phthalocyanine and perylene pigments.

* * * * *